United States Patent
Kim et al.

(10) Patent No.: US 10,287,342 B2
(45) Date of Patent: May 14, 2019

(54) POLYPEPTIDE FOR BINDING TO COMPLEMENT PROTEIN C5A, AND USE OF SAME

(71) Applicant: Korea Advanced Institute of Science and Technology, Daejeon (KR)

(72) Inventors: Hak-Sung Kim, Daejeon (KR); Da Eun Hwang, Daejeon (KR); Jung-Min Choi, Daejeon (KR); Joong-Jae Lee, Daejeon (KR); Woosung Heu, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 114 days.

(21) Appl. No.: 15/500,921

(22) PCT Filed: Aug. 3, 2015

(86) PCT No.: PCT/KR2015/008094
§ 371 (c)(1),
(2) Date: Jan. 31, 2017

(87) PCT Pub. No.: WO2016/018133
PCT Pub. Date: Feb. 4, 2016

(65) Prior Publication Data
US 2017/0218060 A1    Aug. 3, 2017

(30) Foreign Application Priority Data
Aug. 1, 2014 (KR) .................... 10-2014-0098833

(51) Int. Cl.
| | |
|---|---|
| *A61K 39/00* | (2006.01) |
| *A61K 39/02* | (2006.01) |
| *C07H 21/04* | (2006.01) |
| *C07K 16/18* | (2006.01) |
| *C12N 15/62* | (2006.01) |
| *C07K 14/725* | (2006.01) |
| *C07K 14/34* | (2006.01) |
| *A61K 38/00* | (2006.01) |

(52) U.S. Cl.
CPC .............. *C07K 16/18* (2013.01); *C07K 14/34* (2013.01); *C07K 14/7051* (2013.01); *C12N 15/62* (2013.01); *A61K 38/00* (2013.01); *C07K 2318/20* (2013.01)

(58) Field of Classification Search
CPC ........ A61K 39/00; A61K 39/02; C07H 21/02; C07H 21/04
USPC ..... 424/184.1, 185.1, 190.1, 234.1; 530/300, 530/350; 536/23.1, 23.7
See application file for complete search history.

(56) References Cited

FOREIGN PATENT DOCUMENTS

| EP | 2647706 A1 | 10/2013 |
|---|---|---|
| KR | 1020110099600 A | 9/2011 |
| KR | 10-2012-0022453 A | 3/2012 |
| KR | 10-1356075 B1 | 2/2014 |

OTHER PUBLICATIONS

Lee, S., et al., "Design of a Binding Scaffold Based on Variable Lymphocyte Receptors of Jawless Vertebrates by Module Engineering", "Proceedings of the National Academy of Sciences", Feb. 28, 2012, pp. 3299-3304, vol. 109, No. 9.

*Primary Examiner* — Rodney P Swartz
(74) *Attorney, Agent, or Firm* — Hultquist, PLLC; Steven J. Hultquist

(57) ABSTRACT

The present invention relates to novel polypeptide for binding to a complement protein C5a. More particularly, the present invention relates to polypeptide which can be bound to a complement protein C5a and inhibit the activation of same, polynucleotide which codes for the polypeptide, a recombinant vector which comprises the polynucleotide, a recombinant microorganism to which the recombinant vector has been introduced, a method for producing the polypeptide by means of the recombinant microorganism, and a pharmaceutical composition, for treating immune diseases or sepsis, containing the polypeptide. A polypeptide, according to the present invention, can be bound to a complement protein C5a, with higher affinity compared to being bound to a complement protein C5a receptor which is present in nature, and inhibits the activation of same, thus being widely utilized for development of formulation for preventing or treating diseases related to a complement protein C5a.

6 Claims, 8 Drawing Sheets
(8 of 8 Drawing Sheet(s) Filed in Color)
Specification includes a Sequence Listing.

[FIG.1]
[FIG.2]
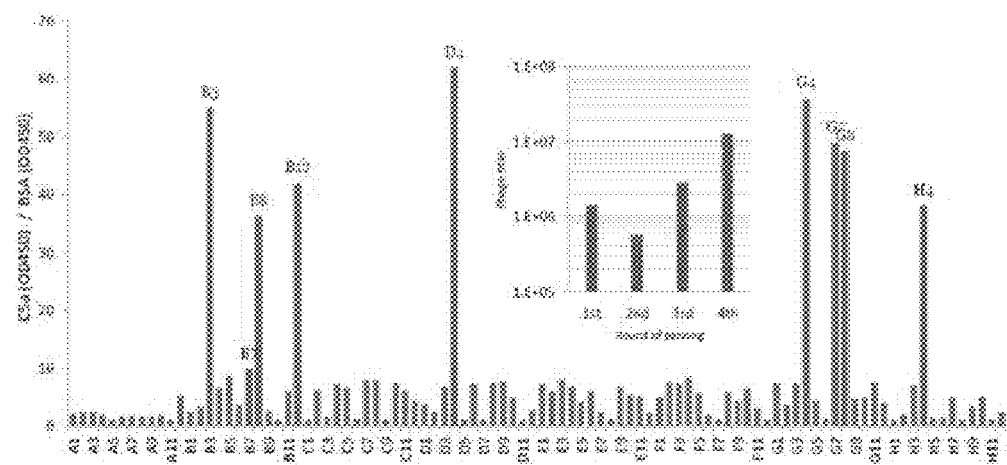
G7

[FIG.3]

G7
G7 : C-loop delete

```
         230        240
G7       EWINKHSGVVRNSAGSV P
G7:C-loop EWINKHSGVVG------ P
delete
```

G7 = SEQ ID NO: 9; G7: C-loop delete = SEQ ID NO: 10

[FIG.6]
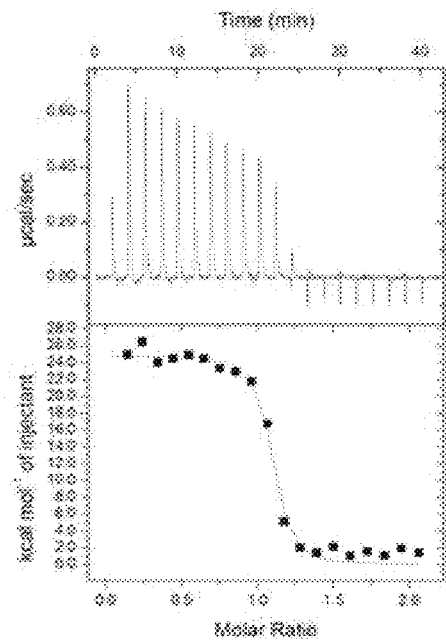
F5
[FIG.7]
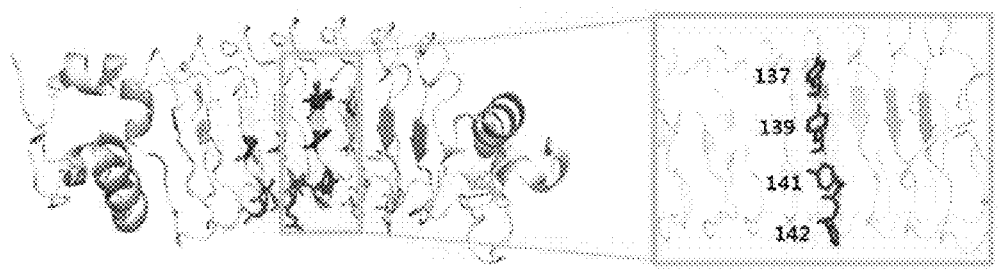

[FIG.8]
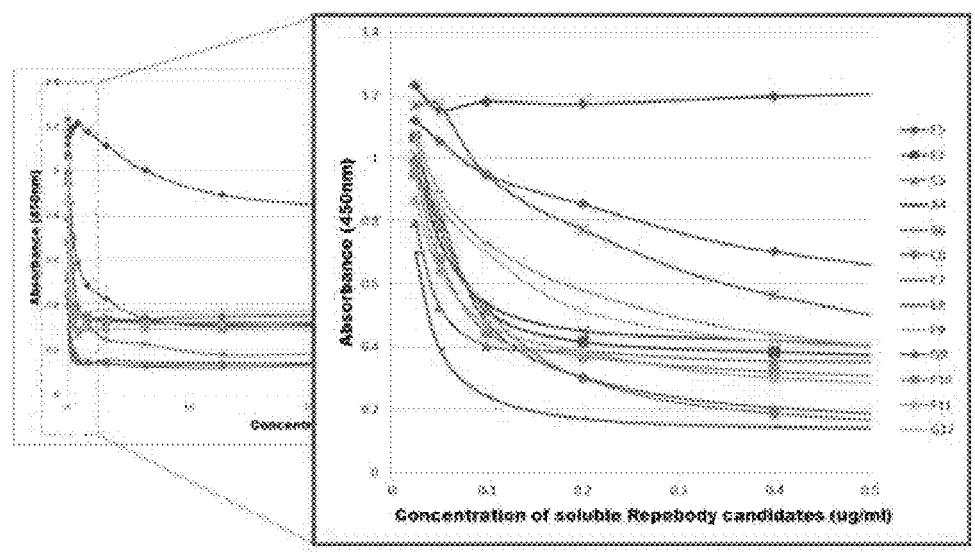

[FIG.9]
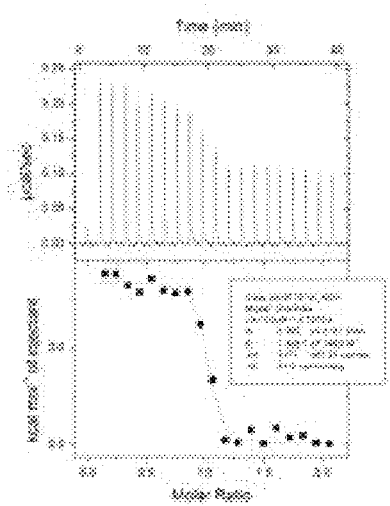
F10
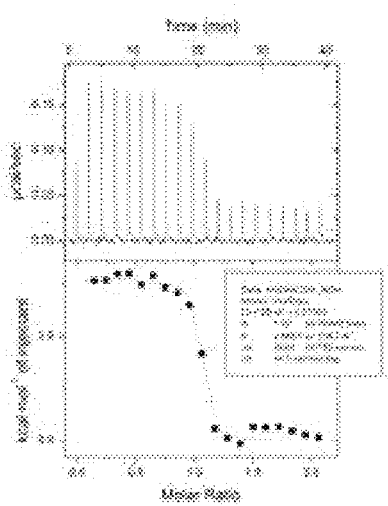
C3
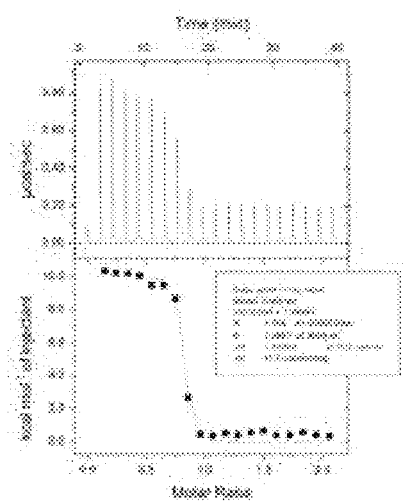
F11
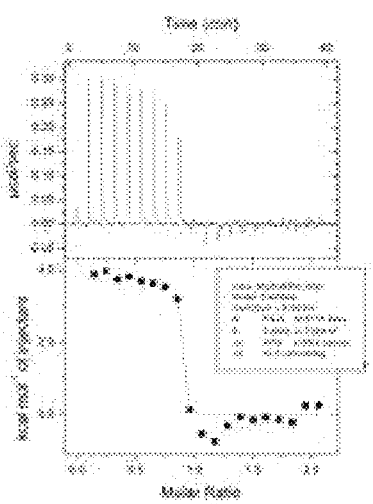
E8

[FIG.10]
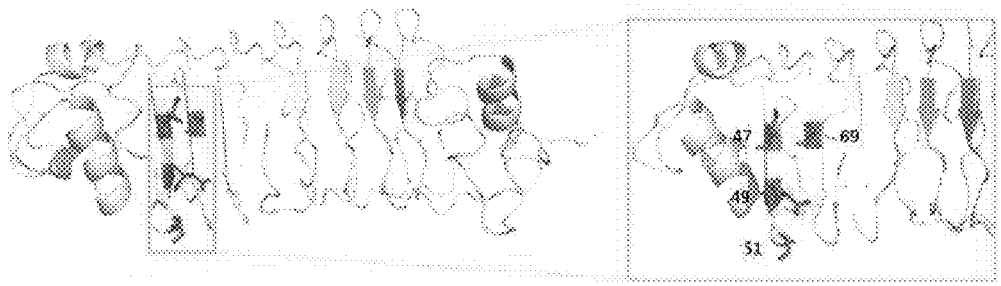
[FIG.11]
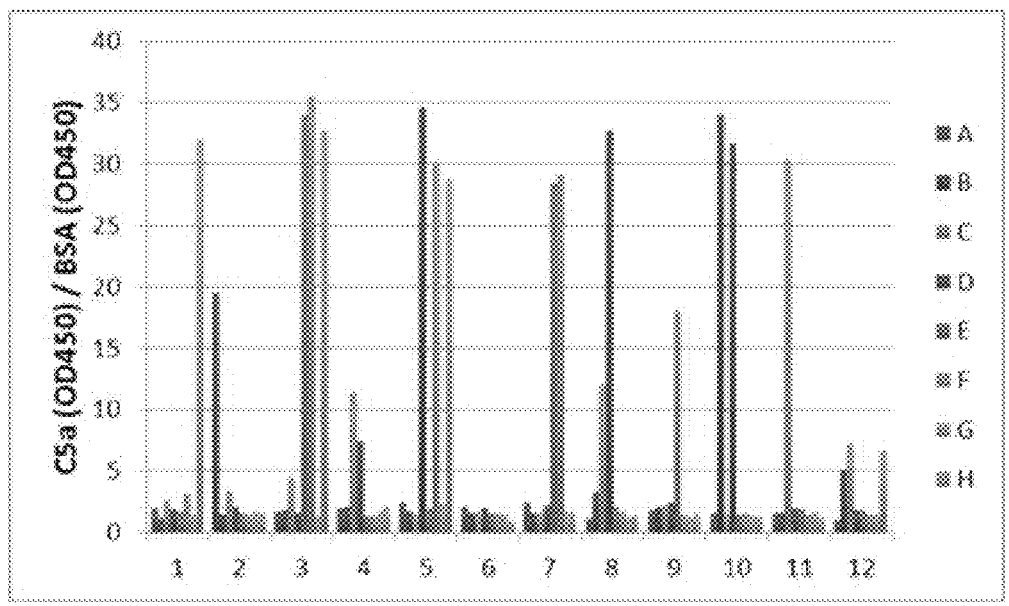

[FIG.12]
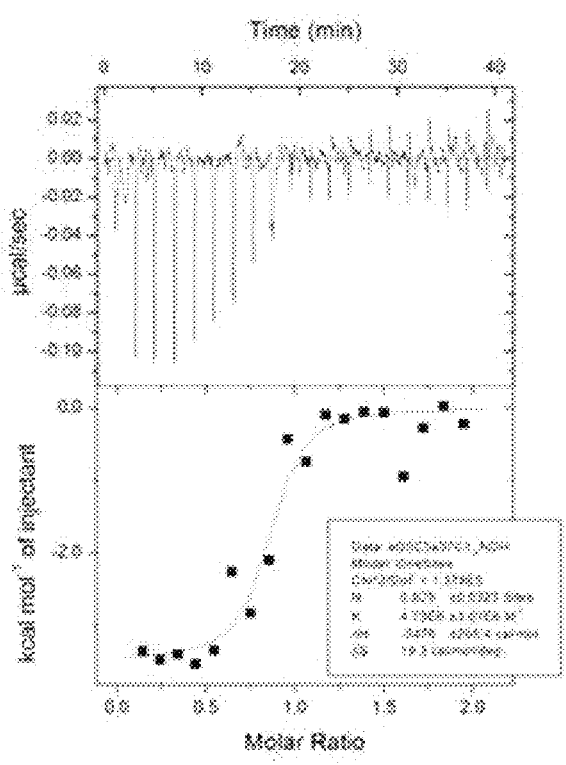
D5

[FIG.13]
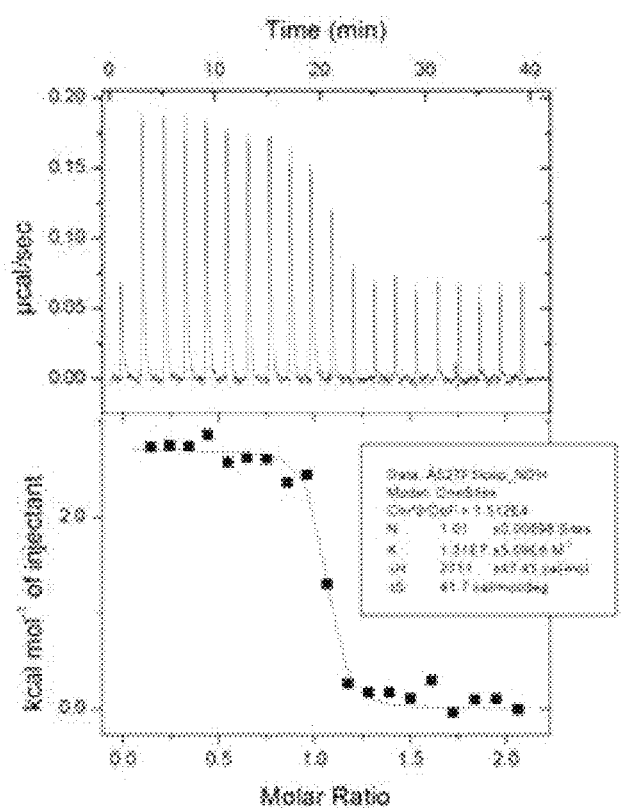
F5 C-loop insertion

POLYPEPTIDE FOR BINDING TO COMPLEMENT PROTEIN C5A, AND USE OF SAME

CROSS-REFERENCE TO RELATED APPLICATIONS

This application is a U.S. national phase under the provisions of 35 U.S.C. § 371 of International Patent Application No. PCT/KR15/08094 filed Aug. 3, 2015, which in turn claims priority of Korean Patent Application No. 10-2014-0098833 filed Aug. 1, 2014. The disclosures of such international patent application and Korean priority patent application are hereby incorporated herein by reference in their respective entireties, for all purposes.

TECHNICAL FIELD

The present invention relates to a novel polypeptide capable of binding to a complement protein C5a, and more particularly, to a polypeptide capable of binding to a complement protein C5a to inhibit an activity thereof, a polynucleotide encoding the polypeptide, a recombinant vector including the polynucleotide, a recombinant microorganism into which the recombinant vector is introduced, a method for producing the polypeptide using the recombinant microorganism, and a pharmaceutical composition for treating an immune disease or sepsis including the polypeptide.

BACKGROUND ART

Proteins are macromolecules that perform maintenance and function of life phenomena, and are responsible for a wide range of biological roles among various materials present in vivo. In order to perform these roles, protein-protein interactions should first be achieved, which is considered to be the basis of all life phenomena. If the protein interactions are not properly regulated, homeostasis in the body is destroyed, resulting in various diseases. Accordingly, various methods for treating diseases by artificially regulating the protein interactions have been studied and developed, and various pharmaceutical products that are actually usable for therapeutic purposes have been successfully developed.

Antibodies are important proteins of an immune response, and perform biological functions through specific interaction with antigens. This specific binding capacity enables a high therapeutic effect without side effects unlike conventional low molecular chemical agents. Therefore, many research institutions and pharmaceutical companies are actively conducting research to develop the antibodies having binding capacity with respect to well-known therapeutic agent targets using a variety of screening techniques. Due to the low side effects and high therapeutic efficacy compared to the chemical agents, the development of antibody therapeutic agents have been heavily invested by global pharmaceutical companies and biotechnology companies, and thus, a number of antibody therapeutic agents are currently used in clinical practice, and many therapeutic candidates are in clinical trials. In addition, it is widely used in various fields such as separation and purification of biomaterials and molecular medical diagnosis technology, etc., as well as for therapeutic purposes. However, in spite of these advantages, there are problems in that production cost is high, it is difficult to escape the existing patent barriers, it is difficult to penetrate into cells due to large molecular weight, and therapeutic effects of patients are not actually high as expected. Accordingly, in recent years, development of artificial antibodies for replacing the antibody therapeutic agents has been actively conducted. A number of researches have revealed that these artificial antibody scaffold proteins are largely improved in efficiency of penetration into cancer tissues unlike the antibody therapeutic agents, and as a result, therapeutic effects are able to be improved.

Under these circumstances, the present inventors have successfully developed a repebody which is a non-antibody protein scaffold capable of replacing the conventional antibodies. The repebody refers to a polypeptide optimized by consensus design through fusion based on similarity between an N-terminal of internalin and a variable lymphocyte receptor (VLR) structure having a leucine-rich repeat (LRR) structure. The repebody has a size that is about ⅕ a size of the antibody, and is mass-produced in *Escherichia coli*, and has almost no immunogenicity as a result of animal tests. Further, the repebody has significantly excellent stability against heat and pH, and is able to very easily increase binding capacity to a target up to a pico-mole level, and has remarkably superior specificity to the target.

Meanwhile, the complement protein C5a is known to be a disease inducer causing immune diseases such as asthma, rheumatoid arthritis, and lupus. In particular, the complement protein C5a receives attention as a main target in the treatment of sepsis, which is a disease that shows addition or causes an infection in the whole body due to toxic materials produced by propagation and reproduction of various germs in blood. The sepsis is known worldwide as a major cause of intensive care unit (ICU) morbidity and mortality. In the United States, there are 750,000 sepsis patients each year, and in Korea, very high incidence is shown even though there is no accurate statistics. The mortality rate is also very high, about 40%. However, a therapeutic agent which was FDA-approved in 2001, was withdrawn from the market in 2011, and there are still very few effective treatment methods or therapeutic materials. Therefore, research on the development of a therapeutic agent targeting the complement protein C5a as a therapeutic agent for sepsis has been actively conducted.

The present inventors have successfully produced a specific protein binder for various disease-related target proteins using the above-described repebody scaffold, and have verified to have a biological inhibition effect based on cell-based methods. However, this application study thereof is only in the beginning stage, and thus, further research is actively underway.

Therefore, the present inventors have made efforts to develop a protein that specifically binds to the complement protein C5a, which is known to be related to various immune diseases using the above-described repebody scaffold, and as a result, selected a novel polypeptide having a specific binding capacity to the complement protein C5a based on random mutation library constructed through modularity which is a structural characteristic of the repebody and overall structure analysis, and confirmed that the binding strength of the complement protein C5a to the polypeptide is higher than that of a complement protein C5a receptor which is present in nature, and completed the present invention.

DISCLOSURE

Technical Problem

An object of the present invention is to provide a polypeptide capable of specifically and strongly binding to a complement protein C5a to inhibit an activity thereof.

Another object of the present invention is to provide a polynucleotide encoding the polypeptide, a recombinant vector including the polynucleotide, and a recombinant microorganism into which the recombinant vector is introduced.

Still another object of the present invention is to provide a method for producing the polynucleotide using the recombinant microorganism.

Still another object of the present invention is to provide a pharmaceutical composition for treating an immune disease or sepsis including the polypeptide as an active ingredient.

Technical Solution

In order to achieve the foregoing objects, the present invention provides a polypeptide that specifically binds to a complement protein C5a, fused with an N-terminal of an internalin B protein, a modified repeat module of a VLR protein, and a C-terminal of the VLR protein.

In addition, the present invention provides a polynucleotide encoding the polypeptide, a recombinant vector including the polynucleotide, and a recombinant microorganism into which the recombinant vector is introduced.

Further, the present invention provides a method for producing a polypeptide that specifically binds to a complement protein C5a, the method including (a) culturing the recombinant microorganism to obtain a culture; and (b) recovering the polypeptide from the cultured recombinant microorganism or the culture.

In addition, the present invention provides a pharmaceutical composition for treating an immune disease or sepsis including the polypeptide as an active ingredient.

DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows results of bio-panning of a phage display with respect to a complement protein C5a, using a phage library constructed in the above-described related art patent (KR2012-0019927), wherein a binding signal was normalized by an enzyme linked immunosorbent assay (ELISA) with respect to the complement protein C5a versus BSA, which is defined by a repebody clone having a specific binding capacity to a clone of which a signal is increased by 10 times or more.

FIG. 2 shows results of dissociation constants of G7 which is a clone showing the highest binding capacity among the clones obtained in FIG. 1, measured using an isothermal titration calorimetry (ITC), wherein it was confirmed that the clone had a low binding capacity of 2.8 M with respect to the complement protein C5a.

FIG. 3 shows a sequence in which a C-terminal loop, which is considered to interfere with the binding between the repebody and the complement protein C5a in the G7, which is the selected clone in FIG. 2, is removed.

FIG. 4 shows amino acid residues present in LRRV5 module and LRRVe module in which a second library is constructed based on the G7 that is the clone primarily selected to increase the binding capacity.

FIG. 5 shows results of bio-panning of the phage display using the second library, wherein a binding signal was normalized by an enzyme linked immunosorbent assay (ELISA) with respect to the complement protein C5a versus BSA, which is defined by a repebody clone having an increased binding capacity with respect to a clone of which a signal is increased by 5 times or more. In FIG. 5, "A", "B", "C", "D", "E", "F", "G", and "H" are identifiers that classify the respective screening groups, and otherwise have no independent significance.

FIG. 6 shows results of dissociation constants of F5 which is a clone showing the highest binding capacity among the clones obtained in FIG. 5, measured using an isothermal titration calorimetry (ITC), wherein it was confirmed that the clone had a binding capacity of 56 nM with respect to the complement protein C5a. This binding capacity is increased by about 53 times as compared to that of the G7 clone before the binding capacity is increased.

FIG. 7 shows amino acid residues present in LRRV3 module in which a third library is constructed based on the F5 that is the clone secondarily selected to increase the binding capacity.

FIG. 8 shows results of bio-panning of the phage display using the third library. In the drawing, a binding signal was normalized by an enzyme linked immunosorbent assay (ELISA) with respect to the complement protein C5a versus BSA, which is defined by a repebody clone having an increased binding capacity with respect to a clone of which a signal is increased by 30 times or more.

FIG. 9 shows results of dissociation constants of clones having an increased binding capacity than that of F5, among the clones obtained in FIG. 8, measured using an isothermal titration calorimetry. The clone E8 has the highest binding capacity which is about 1.9 nM with respect to the complement protein C5a, which is increased by about 29 times as compared to that of the F5 clone before the binding capacity is increased.

FIG. 10 shows amino acid residues present in LRR1 module and LRRV1 module in which a final library is constructed based on the E8 that is the clone tertiarily selected to increase the binding capacity.

FIG. 11 shows results of bio-panning of the phage display using the final library, wherein a binding signal was normalized by an enzyme linked immunosorbent assay (ELISA) with respect to the complement protein C5a versus BSA, which is defined by a repebody clone having an increased binding capacity with respect to a clone of which a signal is increased by 15 times or more.

FIG. 12 shows results of dissociation constants of a clone in which a C-terminal loop is inserted into the clone F5 with respect to D5 which is a clone having an increased binding capacity than that of E8, among the clones obtained in FIG. 11, measured using a displacement isothermal titration calorimetry.

FIG. 13 shows results of binding capacity with the complement protein C5a after inserting the C-terminal loop into the clone F5 showing the highest binding capacity among the clones obtained in FIG. 5.

BEST MODE

Unless defined otherwise, all the technical and scientific terms used herein have the same meanings as those generally understood by persons skilled in the art to which the present invention pertains. Generally, the nomenclature used herein are well known and commonly employed in the art.

In the development of a novel polypeptide capable of specifically binding to complement protein C5a in the present invention, a polypeptide having high binding specificity and capable of mass production has been discovered. A library randomly including repeat modules of polypeptide, fused with an N-terminal of an internalin B protein and a leucine-rich repeat (LRR) protein portion of a variable lymphocyte receptor (VLR) protein was constructed by using a polynucleotide encoding the novel polypeptide, a recombinant vector including the polynucleotide, and a recombinant microorganism into which the recombinant vector is introduced. Then, a manner for increasing binding capacity of a repebody to the complement protein C5a using a module-based method was performed, and a novel polypeptide having high binding capacity to the complement protein C5a was identified.

Therefore, in an aspect, the present invention relates to a polypeptide that specifically binds to the complement protein C5a, fused with an N-terminal of an internalin B protein, a modified repeat module of a VLR protein, and a C-terminal of the VLR protein.

In an embodiment of the present invention, a polypeptide including any one amino acid sequence of SEQ ID NOS: 1 to 8 and capable of effectively binding the complement protein C5a was selected.

Term 'complement component C5a' of the present invention refers to a small protein fragment of about 9 kDa, formed from cleavage of the complement protein C5 in a complement activation process. The complement protein C5a is involved in a variety of inflammatory responses such as destruction of mast cells and basophil granules to release of histamine, thereby increasing vascular permeability, and an invitation of leukocytes to promote phagocytosis, etc. In particular, C5a, which is present in the body excessively, causes an excessive immune reaction and causes an abnormal inflammatory reaction, and these phenomena are found in various diseases such as asthma, rheumatoid arthritis, lupus, sepsis, etc.

In the present invention, in order to develop a novel polypeptide capable of specifically binding to the complement protein C5a, a library randomly including repeat modules of polypeptide, fused with an N-terminal of an internalin B protein and a leucine-rich repeat (LRR) protein portion of a variable lymphocyte receptor (VLR) was constructed. The polypeptide included in the library may be encoded by a polynucleotide sequence of SEQ ID NO: 1 described in the Related Art Patent (KR 2012-0019927) by the present inventors or by a polynucleotide sequence having a homology of 75%, preferably 85%, more preferably 90%, more preferably 95% or more with the corresponding polynucleotide sequence. In addition, the library may have a phagemid form including the polynucleotide.

Term "phagemid" in the present invention refers to a circular polynucleotide molecule derived from a phage which is a virus having *E. coli* as a host, and includes sequences of proteins and surface-proteins required for propagation and proliferation. A recombinant phagemid may be produced by using gene recombinant technologies well known in the art, and site-specific DNA cleavage and linkage may be performed by using enzymes generally known in the art, etc. The phagemid may include a signal sequence or a leader sequence for secretion in addition to expression regulatory elements such as a promoter, an operator, an initiation codon, a stop codon, an enhancer, etc., and may be mainly used in a method for labeling a desired protein on a phage surface by fusion with a surface protein of phage. The promoter of the phagemid is inducible, and may include a selective marker for selecting a host cell. For an object of the present invention, the phagemid may be a polynucleotide which encodes SEQ ID NO: 2 described in the Related Art Patent (KR 2012-0019927) that includes MalEss, DsbAss or PelBss which is a signal sequence or a leader sequence for expressing and secreting the polynucleotide encoding the polypeptide included in the library, and that includes a polynucleotide encoding a histidine-tag for confirming expression of a recombinant protein on a surface of the phage, and gp3 domain which is a kind of a surface protein of M13 phage for expression on the surface of the phage, but the present invention is not particularly limited thereto.

In the present invention, a novel polypeptide (SEQ ID NO: 1) having a repebody form which has an excellent binding capacity to the complement protein C5a was selected by using a phage display method using the library including the phagemid (FIG. 1). However, these selected polypeptides have a lower level of binding capacity to the complement protein C5a than that of a complement component 5a receptor which is present in nature (FIG. 2), and thus, it was attempted to add mutants to the selected polypeptides to produce mutant polypeptides having improved binding capacity to the complement protein C5. To this end, according to judgment that a loop of a C-terminal portion of the selected SEQ ID NO: 1 polypeptide may interfere with a binding of the repebody and the complement protein C5a, a total of 8 amino acids were firstly removed from arginine which is an amino acid No. 239 corresponding to the loop up to alanine which is an amino acid No. 246, and two glycines were inserted (FIG. 3). In addition, a second library was constructed by mutating four amino acid residues located in LRRV5 module and three amino acid residues located in LRRVe module with respect to the selected SEQ ID NO: 1 (FIG. 4), and a novel polypeptide (SEQ ID NO: 2) having increased binding capacity to the complement protein C5a was secondly selected by using a phage display method using the second library. Next, a third library was constructed by mutating the LRRV4 module in the same manner based on the polypeptide of SEQ ID NO: 2 that is the above-selected clone (FIG. 7), and a novel polypeptide (SEQ ID NOS: 3 to 6) having a repebody form which has a more increased binding capacity to the complement protein C5a was tertiarily selected from the third library by using a phage display method. For the respective selected clones, binding capacity to the complement protein C5a was measured by using an isothermal titration calorimetry (FIG. 9). Among the clones, the polypeptide of SEQ ID NO: 6 was found to be a clone having the highest binding capacity (1.9 nM) to the complement protein C5a. However, the polypeptide that binds to the selected complement protein C5a is expected to have low biological efficacy since it has a lower binding capacity than that of the complement protein C5a receptor which is present in nature. Accordingly, the present inventors constructed a fourth library obtained by mutating a total of four amino acid residues present in the LRR1 and LRRV1 modules based on SEQ ID NO: 6 to secure a repebody having further improved binding ability with the complement protein C5a and having a biological effect at the same time. A novel polypeptide (SEQ ID NO: 7) having a repebody in the form which has a more increased binding capacity (about 78 pM) to complement protein C5a was finally selected by using a phage display method using the fourth library.

Then, in order to confirm whether the C-terminal loop interferes with the binding between the repebody and the complement protein C5a, the binding force of the polypeptide (SEQ ID NO: 8) in which the C-terminal loop was re-inserted into the original position of the polypeptide of SEQ ID NO: 2 was measured (FIG. 13). As a result, it was confirmed that the polypeptide had a binding capacity of about 76 nM, which could be appreciated that the binding capacity was reduced by about 20 nM as compared to the repebody without the C-terminal loop.

Term: "internalin B protein" in the present invention refers to a kind of the LRR family protein expressed in a *Listeria* strain, and it is known that the internalin B protein is stably expressed even in microorganisms due to an N-terminal structure that is different from that of other LRR family proteins in which other hydrophobic cores are uniformly distributed through the entire molecule. Since the N-terminal of the internalin protein, which is the most important for folding the repeat module, is derived from a microorganism and has a more stable structure including an alpha-helix, the internalin protein is effectively usable for stable expression of the LRR family proteins in the microorganisms.

Term: "N-terminal of the internalin protein" of the present invention refers to an N-terminal of the internalin protein required for solubility expression and folding of the protein, and means an alpha-helix capping motif and a repeat module of the internalin protein. The N-terminal of the internalin protein may include, without limitation, any N-terminal of the internalin protein required for solubility expression and folding of the protein, and may include, for example, the alpha-helix capping motif "ETITVSTPIKQIFPDDAFAETI-KANLKKKSVTDAVTQNE" (SEQ ID NO: 11) and the repeat module. Preferably, the repeat module pattern may include "LxxLxxLxLxxN" (SEQ ID NO: 12). L in the repeat module pattern means alanine, glycine, phenylalanine, tyrosine, leucine, isoleucine, valine, or tryptophan; N in the repeat module pattern means asparagine, glutamine, serine, cysteine or threonine, and x in the repeat module pattern means hydrophilic amino acid. As the N-terminal of the internalin protein, an N-terminal having a high structural similarity may be selected depending on types of LRR family protein that is capable of being fused, and the most stable amino acid may be selected through calculation of binding energy, etc., thereby modifying amino acids of the corresponding module.

Term "variable lymphocyte receptor (VLR)" of the present invention means a kind of the LRR family protein expressed in a hagfish and a lamprey, and may be effectively used for a framework capable of binding to various antigenic substances as a protein that performs an immunological function in the hagfish and the lamprey. The polypeptide fused with the N-terminal of the internalin B protein and the VLR protein has an increased solubility and an increased expression amount as compared to those of the VLR protein in which the internalin B protein is not fused, which is usable for producing a novel protein therapeutic agent based on the polypeptide.

Term: "leucine rich repeat (LRR) protein" of the present invention refers to a protein formed by combination of modules in which leucine is repeated at a predetermined position, (i) one or more LRR repeat modules are provided therewith, (ii) the LRR repeat module includes 20 to 30 amino acids, (iii) the LRR repeat module has "LxxLxxLx-LxxN" as a conservation pattern, wherein L means hydrophobic amino acids such as alanine, glycine, phenylalanine, tyrosine, leucine, isoleucine, valine, and tryptophan; N means asparagine, glutamine, serine, cysteine or threonine and x means any amino acid, and (iv) the LRR family protein means a protein having a three dimensional structure like a horseshoe. The LRR family protein of the present invention may include all variants not only having sequences that are already known or that are found using mRNA or cDNA newly derived in a living body, but also having sequences that are unknown in nature through designs such as a consensus design, etc., and including the framework structure of the repeat module.

Term: "repebody" of the present invention is a polypeptide optimized by consensus design through fusion based on similarity between the VLR structure and the N-terminal of internalin having the leucine-rich repeat (LRR) structure. The repebody protein may be structurally divided into a concave region and a convex region (FIG. 4). Here, it is known that the concave region has high sequence diversity and is important in protein interaction. On the contrary, the convex region serves to stably maintain the entire structure of protein based on the highly conserved sequence. The repebody protein may include all fusion LRR family proteins obtained by improving solubility expression and biophysical properties of all proteins belonging to the LRR family having the repeat module by the above-described method.

In another aspect, the present invention provides a polynucleotide encoding the polypeptide, a recombinant vector including the polynucleotide, and a recombinant microorganism into which the recombinant vector is introduced.

The polynucleotide provided in the present invention may be a polynucleotide encoding any one amino acid sequence of SEQ ID NOS: 1 to 8, and may be a polynucleotide having a base sequence having a homology of 70% or more, more preferably 80% or more, and more preferably 90% or more, with the polynucleotide, but is not particularly limited thereto.

Term: "vector" of the present invention may be a DNA product containing a base sequence of polynucleotide encoding a target protein that is operably linked to an appropriate regulation sequence so as to express the target protein in a suitable host cell. The regulation sequence includes a promoter capable of initiating transcription, any operator sequence for modulating such transcription, a sequence encoding a suitable mRNA ribosome binding site, and a sequence controlling termination of transcription and translation. The vector may be transfected into a suitable host, and then may be replicated or may perform functions regardless of the host genome, and may be integrated into a genome itself.

The vector used in the present invention is not particularly limited as long as it is capable of being replicated in host cells, and may be any vector known in the art. Examples of the vector that is generally used may include plasmid, phagemid, cosmid, virus, and bacteriophage in a natural state or in a recombinant state. For example, as the phage vector or the cosmid vector, pWE15, M13, MBL3, MBL4, IXII, ASHII, APII, t10, t11, Charon4A, and Charon21A, etc., may be used, and as the plasmid vector, pBR-based, pUC-based, pBluescriptII-based, pGEM-based, pTZ-based, pCL-based and pET-based, etc., may be used. The vector usable in the present invention is not particularly limited, but may be any known expression vector. Preferably, pACYC177, pACYC184, pCL, pECCG117, pUC19, pBR322, pMW118, pCC1BAC, pET-21a, pET-32a vectors, etc., may be used. The pET-21a vector and the pET-32a vector are the most preferably usable.

Term: "recombinant microorganism" of the present invention means a transfected cell in which a vector having a gene encoding one or more target proteins is introduced into a host cell to express the target proteins, and may be all cells such as eukaryotic cells, prokaryotic cells, etc. The recombinant microorganism may include bacteria cells such as *E. coli, streptomyces, salmonella typhimurium*, etc.; yeast cells; fungal cells such as *pichia pastoris*, etc.; insect cells such as *drosophila, spodoptera* Sf9 cell, etc.; animal cells such as CHO, COS, NSO, 293, bow melanoma cell, etc.; or plant cells, but the present invention is not particularly limited thereto. The host cell usable in the present invention is not particularly limited, but preferably, *E. coli* may be used as the host cell. *E. coli* BL21 (DE3) and Origami B (DE3) may be the most preferably used as the host cell.

Term "recombination" in the present invention means that a vector including polynucleotide encoding a target protein is introduced into a host cell so that the protein encoded by the polynucleotide is capable of being expressed in the host cell. The recombinant polynucleotide may be any one regardless of the position as long as the polynucleotide is capable of being expressed in the host cell, regardless of the matter that the polynucleotide is inserted and positioned into chromosome of the host cell or positioned on an outer portion of the chromosome. In addition, the polynucleotide includes DNA and RNA encoding the target protein. The polynucleotide may be introduced with any shape as long as the polynucleotide is capable of being introduced into the host cell to be expressed. For example, the polynucleotide may be introduced into the host cell as an expression cassette form which is a gene structure including all factors required for self expression. The expression cassette may include a promoter, a transcription termination signal, a ribosome binding site, and a translation termination signal that may be operably linked to the polynucleotide. The expression cassette may be an expression vector performing self-replication. In addition, the polynucleotide may be introduced into the host cell as itself to be operably linked to the sequence required for expression in the host cell.

In still another aspect, the present invention relates to a method for producing a polypeptide that specifically binds to a complement protein C5a, the method including (a) culturing the recombinant microorganism to obtain a culture; and (b) recovering the polypeptide from the cultured recombinant microorganism or the culture.

In the present invention, the culturing of the recombinant microorganism may be preferably performed by a batch culture method, a continuous culture method, a fed-batch culture, and the like, known in the art, but the present invention not particularly limited thereto, wherein culture conditions are not particularly limited, but specifically, pH may be appropriately adjusted (pH of 5 to 9, preferably pH of 6 to 8, most preferably pH of 6.8) by using a basic compound (for example: sodium hydroxide, potassium hydroxide or ammonia) or an acidic compound (for example, phosphoric acid or sulfuric acid), an aerobic condition may be maintained by introducing oxygen, or an oxygen-containing gas mixture into the culture, and the culturing may be performed at a culture temperature of 20 to 45° C., preferably, 25 to 40° C., for about 10 to 160 hours. The polypeptide produced by the culture may be secreted into the medium or may remain in the cell.

In addition, in a culture medium to be used, as carbon source, sugar and carbohydrate (for example, glucose, sucrose, lactose, fructose, maltose, molasses, starch and cellulose), oil and fat (for example, soybean oil, sunflower seed oil, peanut oil and coconut oil), fatty acid (for example, palmitic acid, stearic acid and linoleic acid), alcohol (for example, glycerol and ethanol) and organic acid (for example, acetic acid), and the like, may be used individually or by mixing. As nitrogen source, nitrogen-containing organic compound (for example, peptone, yeast extract, gravy, malt extract, corn steep liquor, soybean flour and urea), or inorganic compound (for example, ammonium sulfate, ammonium chloride, ammonium phosphate, ammonium carbonate and ammonium nitrate) and the like, may be used individually or by mixing. As phosphorus source, potassium dihydrogen phosphate, dipotassium hydrogen phosphate, sodium-containing salt corresponding thereto, and the like, may be used individually or by mixing. The culture medium may also include essential growth promoting materials such as other metal salts (for example, magnesium sulfate or iron sulfate), amino acids, and vitamins.

In recovering the polypeptide produced in the culturing step of the present invention, it is possible to collect desired polypeptide from a culture solution using suitable methods known in the art according to a culture method, for example, a batch culture method, a continuous culture method, a fed-batch culture, or the like.

In still another aspect, the present invention relates to a pharmaceutical composition for treating an immune disease or sepsis including the polypeptide as an active ingredient.

In the present invention, the immune disease includes asthma, rheumatism, arthritis and lupus.

The pharmaceutical composition for treatment including the polypeptide of the present invention may further include suitable excipients and diluents that are generally used in production of a pharmaceutical composition. In addition, the pharmaceutical composition including the polypeptide according to the present invention may be formulated to be used in forms of oral formulations such as powders, granules, tablets, capsules, suspensions, emulsions, syrups and aerosols, etc., external preparations, suppositories, and sterilized injection solutions, according to general methods, respectively.

Examples of carriers, excipients and diluents that may be included in the composition including the polypeptide may include lactose, dextrose, sucrose, sorbitol, mannitol, xylitol, maltitol, starch, glycerin, starch, acacia rubber, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate and mineral oil.

In the formulation, the diluents or excipients that are generally used, such as fillers, extenders, binders, wetting agents, disintegrants, surfactants, etc., may be used for preparation. Solid preparations for oral administration include tablets, pills, powders, granules, capsules, etc., and such a solid preparation may be prepared by mixing at least one excipient such as starch, calcium carbonate, sucrose or lactose, gelatin, etc., in the polypeptide. In addition, lubricants such as magnesium stearate and talc may also be used in addition to simple excipients. Liquid preparations for oral administration include suspensions, solutions, emulsions, syrups, and the like, and may include various excipients, for example, wetting agents, sweeteners, aromatics, preservatives, and the like, in addition to generally used simple diluents such as water, liquid paraffin, and the like. Preparations for parenteral administration include sterilized aqueous solutions, non-aqueous agents, suspensions, emulsions, freeze-dried preparations, and suppositories. Examples of the non-aqueous agents and the suspensions may include propylene glycol, polyethylene glycol, vegetable oil such as olive oil, injectable ester such as ethyl oleate, and the like. As a suppository base, witepsol, macrogol, Tween 61, cocoa butter, laurinum, glycerogelatin, etc., may be used. In addition, coloring agents that are permitted to add to pharmaceutical products are used, and mating agents such as cocoa powder, peppermint, oriental acid, peppermint oil, camphol, cinnamon powder, etc., are used. These tablets do not exclude coatings, for example, coatings with sugar or gelatin, and other suitable coatings as needed, in the case of granules.

In addition, when the composition of the present invention is prepared into an injection, a pH adjusting agent, a buffer, a stabilizer, a preservative, etc., may be added as required, to prepare subcutaneous, intramuscular, intravenous injections by general methods.

A used amount of the polypeptide-containing composition of the present invention may vary depending on the age, sex, and body weight of the patient. In general, the composition may be administered one to three times per day at an amount of 5 to 500 mg/kg, preferably 100 to 250 mg/kg. An administration amount thereof may be increased or decreased depending on an administration route, a degree of disease, sex, weight, age, etc. Therefore, the administration amount is not intended to limit the scope of the invention in any aspects.

Hereinafter, the present invention is described in detail with reference to Examples. These Examples are only provided to specifically explain the present invention, and it will be obvious to those skilled in the art that the technical scope of the present invention is not construed to be limited to these Examples.

Example 1 Selection of Polypeptide that Specifically Binds to Complement Protein C5a Through Random Phage Library Example 1-1: Construction of Repebody Library Based on Protein Structure The repebody has modularity in which repeat units having preserved leucine sequence are continuously connected to maintain an entire protein structure, and a structural characteristic classified into a concave region and a convex region due to curvature of a shape of the entire structure, like the LRR proteins present in the natural world. In addition, the repebody is divided into the concave region that recognizes biomolecules and the convex region that is important to maintain the structure. In the concave region, a hypervariable region such as a complementarity determining region (CDR) of an antibody is positioned, which mediates protein-protein interaction. In addition, the convex region plays an important role in maintaining the entire structure of the LRR based on well-conserved sequences. The protein structure of the repebody was analyzed to design a random library in the following manner.

In detail, six amino acid residues Nos. 91, 93, 94, 115, 117, and 118 positioned in the concave region of two consecutive mutation modules (LRRV modules 2 and 3) positioned in an amine group terminal direction were selected in order to escape sterical hindrance by an removal of carboxy terminal loop (C-term loop) from template scaffold (PDB: 3RFS). Then, a mutagenic primer for constructing a library was synthesized by substituting the selected amino acids with a degenerate codon of NNK, and constructing base sequences of the remaining convex region to include a silent mutation.

Next, overlap PCR was performed on the two modules using the above primers to obtain a library DNA, and the library DNA was inserted into the phagemid pBEL118M to secure a final library phagemid.

The secured library was introduced into *E. coli* XL1-Blue by electroporation to obtain a recombinant microorganism, and thus, a library having synthetic diversity of about $1.8 \times 10^8$ was constructed.

Example 1-2: Selection of Polypeptide that Bind to Complement Protein C5a Through Panning of Repebody Library Polypeptides capable of binding to the complement protein C5a were selected by using the library constructed in Example 1-1, and purified. In order to select candidates that are capable of binding to the complement protein C5a, an immuno-tube was coated with the complement protein C5a at a concentration of 100 ml at 4° C. for 12 hours. The coated immuno-tube was washed three times with PBS, and blocked with PBS solution (TPBSA) including 1% BSA and 0.05% Tween 20 at 4° C. for 2 hours. Then, the purified phage was added to the coated immune tube at a concentration of $10^{12}$ cfu/ml, and reacted at room temperature for 2 hours. After the reaction was completed, the tube was washed 5 times with PBS solution (TPBS) including 0.05% Tween 20 and washed 2 times with PBS for 2 minutes in total. Finally, 1 ml of 0.2 M Glycine-HCl (pH 2.2) was added to the immuno-tube, followed by reaction at room temperature for 13 minutes, thereby eluting a phage expressing the repebody candidate capable of binding to the complement protein C5a on a surface. The eluate was neutralized by adding 60 ml of 1.0 M Tris-HCl (pH 9.0), and added to a 10 ml of *E. coli* XL1-Blue solution (OD600=0.5) as a host cell, and then, a bio-panning process in which the cell is spread on a 2×YT plate was repeated four times in the same manner. As a result, it was confirmed from each panning process that the phage that specifically binds to the complement protein C5a was concentrated. Analysis of the above result indicated that the library phage binding to the complement protein C5a was specifically increased.

Example 1-3: Confirmation Whether Selected Repebody Specifically Binds to Complement Protein C5a, and Sequence Analysis ELISA (enzyme linked immunosorbent assay) was performed on the phage selected through the method of Example 1-2 using a 96-well plate coated with complement protein C5a and BSA, and 9 repebody candidates having absorbance (OD450) of the complement protein C5a 10 times or more higher than BSA were selected (FIG. 1). Respective amino acid sequences thereof were confirmed, and clones having the same amino acid sequence were excluded. As a result, three kinds of the repebody sequences were confirmed in the selected phage, and a dissociation constant with respect to the complement protein C5a was measured on the three kinds of repebodies, using an isothermal titration calorimetry. As a result, it was confirmed that only the clone G7 specifically bonded to the complement protein C5a (FIG. 2). In G7, it was confirmed that isoleucine, which is amino acid No. 91, was substituted with phenylalanine, threonine, which is amino acid No. 93, was substituted with aspartic acid, glycine, which is amino acid No. 94, was substituted with phenylalanine, valine, which is amino acid No. 115, was substituted with tyrosine, valine, which is amino acid No. 117, was substituted with serine, and glutamic acid, which is amino acid No. 118, was substituted with proline (SEQ ID NO: 1).

Analysis of the above result indicated that there was a residue that plays an important role in binding to the complement protein C5a.

Example 2: Enhancement of Binding Capacity of Repebody to Complement Protein C5a Using Module-Based Method The method for increasing module-based affinity described in the present invention was performed according to the Related Art Patent (KR2012-0019927). This method is a technique that is usable universally for proteins having repeat modules, and is successfully reproduced herein to be capable of designing a protein having a high level of affinity.

Example 2-1: Construction of Additional Library Using Module and Confirm Increase of Binding Capacity A dissociation constant with respect to the complement protein C5a of G7, which is a clone that specifically binds to the complement protein C5a as confirmed from the result of Example 1-3, was 2.8 M (FIG. 2). However, a dissociation constant with respect to the complement protein C5a of the complement protein C5a receptor which is present in nature, was about 1.0 nM. Accordingly, it was expected that the activity of the complement protein C5a could not be sufficiently inhibited by the repebody candidates of the present invention.

In order to solve these problems, a mutant having improved binding capacity was attempted to be developed by using an additional library construction method using a module used in the Related Art Patent (KR2012-0019927).

Specifically, from the library for increasing affinity based on a first module, a total of 7 amino acid residues of the LRRV5 and LRRVe modules were mutated (FIG. 4), followed by a total of 4 panning steps, thereby securing F5 (SEQ ID NO: 2) having increased binding capacity, and a dissociation constant thereof was measured using the isothermal titration calorimetry. As a result, it was confirmed that the F5 had the binding capacity of 56 nM to the complement protein C5a (FIG. 6).

On the other hand, to develop a mutant showing a more improved binding capacity, F5 was used as a base polypeptide to mutate four residues of the LRRV4 module (FIG. 7), followed by the same panning process, thereby selecting E8 (SEQ ID NO: 6), and a dissociation constant thereof was measured using the isothermal titration calorimetry. As a result, it was confirmed that the E8 had the binding capacity of 1.9 nM to the complement protein C5a (FIG. 9). This is an improved result by about 29 times as compared to the F5 used as the base polypeptide.

In the third process for enhancing affinity, a library was constructed on a total of four residues of the LRR1 and LRRV1 modules based on the E8 (FIG. 10), and as a result, a clone, D5 (SEQ ID NO: 7) was selected. The binding capacity to the complement protein C5a was confirmed by the isothermal titration calorimetry (FIG. 12), and as a result, it was confirmed that the dissociation constant of the final clone, D5, to the complement protein C5a, was 73 pM, which showed significantly strong binding, and thus, the D5 was secured as the final clone.

From these results, the present inventors have successfully secured the repebody having a higher binding capacity than that of the complement protein C5a receptor which is present in nature, and confirmed that it is the polypeptide having specific binding capacity to the complement protein C5a.

Although specific embodiments of the present invention are described in detail, it will be apparent to those skilled in the art that the specific description is merely desirable exemplary embodiment and should not be construed as limiting the scope of the present invention. Therefore, the substantial scope of the present invention is defined by the accompanying claims and equivalent thereof.

INDUSTRIAL APPLICABILITY

The polypeptide of the present invention is capable of binding to the complement protein C5a with an affinity higher than that of the complement protein C5a receptor which is present in nature, and inhibiting an activity thereof, which is widely utilized for development of preventive agents or therapeutic agents of complement protein C5a-related diseases.

The invention claimed is:

1. A polypeptide capable of binding to a complement protein C5a, comprising the amino acid sequence of any one of SEQ ID NOS: 1, 2 and 4 to 8.

2. The polypeptide capable of binding to complement protein C5a of claim 1, the polypeptide consisting of a non-antibody protein scaffold repebody.

3. A polynucleotide encoding the polypeptide of claim 1.

4. A vector comprising the polynucleotide of claim 3.

5. A recombinant microorganism having introduced therein the polynucleotide of claim 3 or a vector comprising said polynucleotide.

6. A method for preparing a polypeptide capable of binding to complement protein C5a, wherein the method comprises:
   (i) producing the polypeptide by culturing the recombinant microorganism of claim 5; and
   (ii) recovering the produced polypeptide.

* * * * *

SEQUENCE LISTING

<160> NUMBER OF SEQ ID NOS: 12

<210> SEQ ID NO 1
<211> LENGTH: 259
<212> TYPE: PRT
<213> ORGANISM: Artificial Sequence
<220> FEATURE:
<223> OTHER INFORMATION: Repebody-F10

<400> SEQUENCE: 1

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95

Leu Gln Leu Pro Asn Gly Val Phe Asp Lys Leu Thr Asn Leu Lys Glu
            100                 105                 110
```

```
Leu Tyr Leu Ser Pro Asn Gln Leu Gln Ser Leu Pro Asp Gly Val Phe
            115                 120                 125

Asp Lys Leu Thr Asn Leu Thr Ser Leu Gly Leu Asp Phe Asn Gln Leu
        130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                165                 170                 175

Asp Lys Leu Thr Gln Leu Lys Asp Leu Ser Leu Ser Tyr Asn Gln Leu
        180                 185                 190

Lys Ser Val Pro Asp Gly Val Phe Asp Arg Leu Thr Ser Leu Gln Tyr
            195                 200                 205

Ile Trp Leu His Asp Asn Pro Trp Asp Cys Thr Cys Pro Gly Ile Arg
            210                 215                 220

Tyr Leu Ser Glu Trp Ile Asn Lys His Ser Gly Val Val Gly Gly Pro
225                 230                 235                 240

Asp Ser Ala Lys Cys Ser Gly Ser Gly Lys Pro Val Arg Ser Ile Ile
                245                 250                 255

Cys Pro Thr

<210> SEQ ID NO 2
<211> LENGTH: 259
<212> TYPE: PRT
<213> ORGANISM: Artificial Sequence
<220> FEATURE:
<223> OTHER INFORMATION: Repebody-F5

<400> SEQUENCE: 2

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95

Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
            115                 120                 125

Asp Lys Leu Thr Asn Leu Thr Tyr Leu Asn Leu Ala His Asn Gln Leu
        130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                165                 170                 175

Asp Lys Leu Thr Gln Leu Lys Asp Leu Ser Leu Ser Tyr Asn Gln Leu
        180                 185                 190

Lys Ser Val Pro Asp Gly Val Phe Asp Arg Leu Thr Ser Leu Gln Tyr
            195                 200                 205
```

```
Ile Trp Leu His Asp Asn Pro Trp Asp Cys Thr Cys Pro Gly Ile Arg
        210                 215                 220

Tyr Leu Ser Glu Trp Ile Asn Lys His Ser Gly Val Val Gly Gly Pro
225                 230                 235                 240

Asp Ser Ala Lys Cys Ser Gly Ser Gly Lys Pro Val Arg Ser Ile Ile
            245                 250                 255

Cys Pro Thr

<210> SEQ ID NO 3
<211> LENGTH: 259
<212> TYPE: PRT
<213> ORGANISM: Artificial Sequence
<220> FEATURE:
<223> OTHER INFORMATION: Repebody-F10

<400> SEQUENCE: 3

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95

Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
        115                 120                 125

Asp Lys Leu Thr Asn Leu Thr Ser Leu Gly Leu Asp Phe Asn Gln Leu
    130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                165                 170                 175

Asp Lys Leu Thr Gln Leu Lys Asp Leu Ser Leu Ser Tyr Asn Gln Leu
            180                 185                 190

Lys Ser Val Pro Asp Gly Val Phe Asp Arg Leu Thr Ser Leu Gln Tyr
        195                 200                 205

Ile Trp Leu His Asp Asn Pro Trp Asp Cys Thr Cys Pro Gly Ile Arg
    210                 215                 220

Tyr Leu Ser Glu Trp Ile Asn Lys His Ser Gly Val Val Gly Gly Pro
225                 230                 235                 240

Asp Ser Ala Lys Cys Ser Gly Ser Gly Lys Pro Val Arg Ser Ile Ile
                245                 250                 255

Cys Pro Thr

<210> SEQ ID NO 4
<211> LENGTH: 259
<212> TYPE: PRT
<213> ORGANISM: Artificial Sequence
<220> FEATURE:
<223> OTHER INFORMATION: Repebody-C3
```

```
<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95

Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
        115                 120                 125

Asp Lys Leu Thr Asn Leu Thr Ile Leu Gly Leu Asp Leu Asn Gln Leu
    130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                165                 170                 175

Asp Lys Leu Thr Gln Leu Lys Asp Leu Ser Leu Ser Tyr Asn Gln Leu
            180                 185                 190

Lys Ser Val Pro Asp Gly Val Phe Asp Arg Leu Thr Ser Leu Gln Tyr
        195                 200                 205

Ile Trp Leu His Asp Asn Pro Trp Asp Cys Thr Cys Pro Gly Ile Arg
    210                 215                 220

Tyr Leu Ser Glu Trp Ile Asn Lys His Ser Gly Val Val Gly Gly Pro
225                 230                 235                 240

Asp Ser Ala Lys Cys Ser Gly Ser Gly Lys Pro Val Arg Ser Ile Ile
                245                 250                 255

Cys Pro Thr

<210> SEQ ID NO 5
<211> LENGTH: 259
<212> TYPE: PRT
<213> ORGANISM: Artificial Sequence
<220> FEATURE:
<223> OTHER INFORMATION: Repebody-F11

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95
```

-continued

```
Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
            115                 120                 125

Asp Lys Leu Thr Asn Leu Thr Gly Leu Gly Leu Asp Tyr Asn Gln Leu
            130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                    165                 170                 175

Asp Lys Leu Thr Gln Leu Lys Asp Leu Ser Leu Ser Tyr Asn Gln Leu
            180                 185                 190

Lys Ser Val Pro Asp Gly Val Phe Asp Arg Leu Thr Ser Leu Gln Tyr
            195                 200                 205

Ile Trp Leu His Asp Asn Pro Trp Asp Cys Thr Cys Pro Gly Ile Arg
            210                 215                 220

Tyr Leu Ser Glu Trp Ile Asn Lys His Ser Gly Val Val Gly Gly Pro
225                 230                 235                 240

Asp Ser Ala Lys Cys Ser Gly Ser Gly Lys Pro Val Arg Ser Ile Ile
                    245                 250                 255

Cys Pro Thr

<210> SEQ ID NO 6
<211> LENGTH: 259
<212> TYPE: PRT
<213> ORGANISM: Artificial Sequence
<220> FEATURE:
<223> OTHER INFORMATION: Repebody-E8

<400> SEQUENCE: 6

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
        50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                    85                  90                  95

Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
            115                 120                 125

Asp Lys Leu Thr Asn Leu Thr Ile Leu Gly Leu Asp Met Asn Gln Leu
            130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                    165                 170                 175

Asp Lys Leu Thr Gln Leu Lys Asp Leu Ser Leu Ser Tyr Asn Gln Leu
            180                 185                 190
```

Lys Ser Val Pro Asp Gly Val Phe Asp Arg Leu Thr Ser Leu Gln Tyr
            195                 200                 205

Ile Trp Leu His Asp Asn Pro Trp Asp Cys Thr Cys Pro Gly Ile Arg
        210                 215                 220

Tyr Leu Ser Glu Trp Ile Asn Lys His Ser Gly Val Val Gly Pro
225                 230                 235                 240

Asp Ser Ala Lys Cys Ser Gly Ser Gly Lys Pro Val Arg Ser Ile Ile
                245                 250                 255

Cys Pro Thr

<210> SEQ ID NO 7
<211> LENGTH: 259
<212> TYPE: PRT
<213> ORGANISM: Artificial Sequence
<220> FEATURE:
<223> OTHER INFORMATION: Repebody-D5

<400> SEQUENCE: 7

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Glu Gln Ile Lys Ala
        35                  40                  45

Val Asn Lys Asp Ile Lys Ser Val Gln Gly Ile Gln Tyr Leu Pro Asn
    50                  55                  60

Val Arg Tyr Leu Val Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95

Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
        115                 120                 125

Asp Lys Leu Thr Asn Leu Thr Ile Leu Gly Leu Asp Met Asn Gln Leu
    130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                165                 170                 175

Asp Lys Leu Thr Gln Leu Lys Asp Leu Ser Leu Ser Tyr Asn Gln Leu
            180                 185                 190

Lys Ser Val Pro Asp Gly Val Phe Asp Arg Leu Thr Ser Leu Gln Tyr
        195                 200                 205

Ile Trp Leu His Asp Asn Pro Trp Asp Cys Thr Cys Pro Gly Ile Arg
    210                 215                 220

Tyr Leu Ser Glu Trp Ile Asn Lys His Ser Gly Val Val Gly Pro
225                 230                 235                 240

Asp Ser Ala Lys Cys Ser Gly Ser Gly Lys Pro Val Arg Ser Ile Ile
                245                 250                 255

Cys Pro Thr

<210> SEQ ID NO 8
<211> LENGTH: 265
<212> TYPE: PRT
<213> ORGANISM: Artificial Sequence
<220> FEATURE:
<223> OTHER INFORMATION: Repebody-F5 C-loop insertion

<400> SEQUENCE: 8

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Phe Leu Asp Phe Asn Gln
                85                  90                  95

Leu Gln Leu Pro Asn Gly Val Phe Asp Lys Leu Thr Asn Leu Lys Glu
            100                 105                 110

Leu Tyr Leu Ser Pro Asn Gln Leu Gln Ser Leu Pro Asp Gly Val Phe
            115                 120                 125

Asp Lys Leu Thr Asn Leu Thr Tyr Leu Asn Leu Ala His Asn Gln Leu
    130                 135                 140

Gln Ser Leu Pro Lys Gly Val Phe Asp Lys Leu Thr Asn Leu Thr Glu
145                 150                 155                 160

Leu Asp Leu Ser Tyr Asn Gln Leu Gln Ser Leu Pro Lys Gly Val Phe
                165                 170                 175

Asp Lys Leu Thr Gln Leu Lys Asp Leu Ser Leu Ser Tyr Asn Gln Leu
            180                 185                 190

Lys Ser Val Pro Asp Gly Val Phe Asp Arg Leu Thr Ser Leu Gln Tyr
            195                 200                 205

Ile Trp Leu His Asp Asn Pro Trp Asp Cys Thr Cys Pro Gly Ile Arg
            210                 215                 220

Tyr Leu Ser Glu Trp Ile Asn Lys His Ser Gly Val Val Arg Asn Ser
225                 230                 235                 240

Ala Gly Ser Val Ala Pro Asp Ser Ala Lys Cys Ser Gly Ser Gly Lys
            245                 250                 255

Pro Val Arg Ser Ile Ile Cys Pro Thr
            260                 265

<210> SEQ ID NO 9
<211> LENGTH: 19
<212> TYPE: PRT
<213> ORGANISM: Artificial Sequence
<220> FEATURE:
<223> OTHER INFORMATION: clone G7

<400> SEQUENCE: 9

Glu Trp Ile Asn Lys His Ser Gly Val Val Arg Asn Ser Ala Gly Ser
1               5                   10                  15

Val Ala Pro

<210> SEQ ID NO 10
<211> LENGTH: 13
<212> TYPE: PRT
<213> ORGANISM: Artificial Sequence
<220> FEATURE:
<223> OTHER INFORMATION: clone G7: C-loop delete

```
<400> SEQUENCE: 10

Glu Trp Ile Asn Lys His Ser Gly Val Val Gly Gly Pro
1               5                   10

<210> SEQ ID NO 11
<211> LENGTH: 39
<212> TYPE: PRT
<213> ORGANISM: Artificial Sequence
<220> FEATURE:
<223> OTHER INFORMATION: alpha-helix capping motif

<400> SEQUENCE: 11

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu
        35

<210> SEQ ID NO 12
<211> LENGTH: 12
<212> TYPE: PRT
<213> ORGANISM: Artificial Sequence
<220> FEATURE:
<223> OTHER INFORMATION: LxxLxxLxLxxN repeat module pattern
<220> FEATURE:
<221> NAME/KEY: MISC_FEATURE
<222> LOCATION: (1)..(1)
<223> OTHER INFORMATION: Xaa(1...1) is alanine, glycine, phenylalanine,
      tyrosine, leucine, isoleucine, valine, or tryptophan
<220> FEATURE:
<221> NAME/KEY: MISC_FEATURE
<222> LOCATION: (2)..(2)
<223> OTHER INFORMATION: Xaa(2...2) is a hydrophilic amino acid residue
<220> FEATURE:
<221> NAME/KEY: MISC_FEATURE
<222> LOCATION: (3)..(3)
<223> OTHER INFORMATION: Xaa(3...3) is a hydrophilic amino acid residue
<220> FEATURE:
<221> NAME/KEY: MISC_FEATURE
<222> LOCATION: (4)..(4)
<223> OTHER INFORMATION: Xaa(4...4) is alanine, glycine, phenylalanine,
      tyrosine, leucine, isoleucine, valine, or tryptophan
<220> FEATURE:
<221> NAME/KEY: MISC_FEATURE
<222> LOCATION: (5)..(5)
<223> OTHER INFORMATION: Xaa(5...5) is a hydrophilic amino acid residue
<220> FEATURE:
<221> NAME/KEY: MISC_FEATURE
<222> LOCATION: (6)..(6)
<223> OTHER INFORMATION: Xaa(6...6) is a hydrophilic amino acid residue
<220> FEATURE:
<221> NAME/KEY: MISC_FEATURE
<222> LOCATION: (7)..(7)
<223> OTHER INFORMATION: Xaa(7...7) is alanine, glycine, phenylalanine,
      tyrosine, leucine, isoleucine, valine, or tryptophan
<220> FEATURE:
<221> NAME/KEY: MISC_FEATURE
<222> LOCATION: (8)..(8)
<223> OTHER INFORMATION: Xaa(8...8) is a hydrophilic amino acid residue
<220> FEATURE:
<221> NAME/KEY: MISC_FEATURE
<222> LOCATION: (9)..(9)
<223> OTHER INFORMATION: Xaa(9...9) is alanine, glycine, phenylalanine,
      tyrosine, leucine, isoleucine, valine, or tryptophan
<220> FEATURE:
<221> NAME/KEY: MISC_FEATURE
<222> LOCATION: (10)..(10)
<223> OTHER INFORMATION: Xaa(10...10) is a hydrophilic amino acid
      residue
<220> FEATURE:
<221> NAME/KEY: MISC_FEATURE
<222> LOCATION: (11)..(11)
```

```
<223> OTHER INFORMATION: Xaa(11...11) is a hydrophilic amino acid
      residue
<220> FEATURE:
<221> NAME/KEY: MISC_FEATURE
<222> LOCATION: (12)..(12)
<223> OTHER INFORMATION: Xaa(12...12) is asparagine, glutamine, serine,
      cysteine or threonine

<400> SEQUENCE: 12

Xaa Xaa Xaa Xaa Xaa Xaa Xaa Xaa Xaa Xaa Xaa Xaa
1               5                   10
```